United States Patent [19]
Hefner, Jr. et al.

[11] Patent Number: 5,475,155

[45] Date of Patent: Dec. 12, 1995

[54] PREPARATION OF 4,4'-DIHYDROXY-ALPHA'-DIALKYLSTILBENES AND 4,4'-DIHYDROXY-ALPHA'-DIALKYLSTILBENES

[75] Inventors: Robert E. Hefner, Jr.; Maria I. Villarreal; David A. Carr, all of Lake Jackson, Tex.

[73] Assignee: The Dow Chemical Company, Midland, Mich.

[21] Appl. No.: 374,282

[22] Filed: Jan. 18, 1995

Related U.S. Application Data

[62] Division of Ser. No. 162,517, Dec. 3, 1993, Pat. No. 5,414,150.

[51] Int. Cl.$^6$ .......................... C07C 37/20; C07C 39/215
[52] U.S. Cl. .......................... 568/727; 568/716; 568/717; 568/722; 568/728
[58] Field of Search .................................. 568/727, 728, 568/729, 716, 717, 723

[56] References Cited

U.S. PATENT DOCUMENTS

| | | | |
|---|---|---|---|
| 2,623,908 | 12/1952 | Stoesser et al. | 568/727 |
| 2,812,364 | 9/1953 | Farnham et al. | 568/727 |
| 3,221,061 | 11/1965 | Grover et al. | 568/727 |
| 3,326,986 | 6/1967 | Dugan et al. | 568/727 |
| 4,962,163 | 10/1990 | Hefner, Jr. et al. | 525/463 |
| 5,159,030 | 10/1992 | Hefner, Jr. | 525/502 |
| 5,182,340 | 1/1993 | Hefner, Jr. et al. | 525/525 |
| 5,208,306 | 5/1993 | Hefner, Jr. | 526/256 |
| 5,218,062 | 6/1993 | Earls et al. | 525/526 |
| 5,227,452 | 7/1993 | Earls et al. | 528/96 |
| 5,248,360 | 9/1993 | Jones, Jr. et al. | 156/166 |
| 5,262,509 | 11/1993 | Hefner, Jr. et al. | 528/96 |
| 5,264,502 | 11/1993 | Hefner, Jr. et al. | 525/529 |
| 5,266,660 | 11/1993 | Hefner, Jr. et al. | 525/481 |
| 5,268,434 | 12/1993 | Hefner, Jr. et al. | 525/529 |
| 5,270,404 | 12/1993 | Hefner, Jr. et al. | 525/481 |
| 5,270,405 | 12/1993 | Earls et al. | 525/481 |

FOREIGN PATENT DOCUMENTS

| | | | |
|---|---|---|---|
| 1031788 | 6/1958 | Germany | 568/727 |
| 949668 | 2/1964 | United Kingdom | 568/727 |

OTHER PUBLICATIONS

"Synthesis and Characterization of Thermotropic Polyethers and Copolyethers Based on 4,4'-dihydroxy-a-methylstilbene and Flexible Spacers Containing Odd Numbers of Methylene Units" by Percec et al., in *Mol. Cryst. Liq. Cryst.* 1991 vol. 205, pp. 47–66.

"Reactions of a–Halogeno–ketones with Aromatic Compounds. Part I. Reactions of Chloroacetone and 3–Chlorobutanone with Phenol and its Ethers" by Zaheer, et al., in *Journal of Chem. Society*, 1954, Part III, pp. 3045–4712.

Copending Application Serial#07/919,677 (Atty. Docket No. C–37,370–G) filed Jul. 27, 1992 entitled "Mesogenic Epoxy Compounds".

Copending Application Serial#08/099,812 (Atty. Docket No. C–1437,370–I) filed Jul. 29, 1993 entitled "Mesogenic Mono–Epoxy Compounds".

Copending Application Serial#08/069,910 (Atty. Docket No. C–38,341–D) filed Jun. 1, 1993 entitled "Curable Mixtures of Mesogenic Epoxy Resins and Mesogenic Polyamines and Cured Compositions".

Copending application No. 08/015,496 (Atty. Docket No. C–39,329 led "Mesogenic Alkenyl Functional Malemides and Thermosets Thereof".

Copending aplication No. 07/890,735 (Atty. Docket No. C–39,486–B) filed by May 28, 1992 entitled "Mesogenic Glycidyl Amines".

Copending application No. 08/077,480 (Atty. Docket No. C–39,717–A) filed Jun. 14, 1993 entitled "Process For Preparing Composites Based On Oriented Mesogenic Thermoset Resins".

Copending application No. 08/058,100 (Atty. Docket No.C–40,980) filed May 6, 1993 entitled "Bis(Aminophenoxyl)–Alpha–Substitited Stilbenes, Curable Mixtures With Epoxy Resins and Cured Products".

Copending application No. 08/144,982 (Atty. Docket No. C–40,980–A) filed Oct. 27, 1993 entitled "Bis(Aminophenoxy)–Alpha–Substituted Stilbenes, Curable Mixtures With Epoxy Resins and Cured Products".

Copending application No. 07/982,804 (Atty. Docket No. C–39,949) filed Nov. 30, 1992 entitled "Nitro Group Terminated Mesogenic Epoxy Resin Adducts".

Copending Application Serial No. 08/154,805 (Atty. Docket No. C–39,949–A) filed Nov. 18, 1993 entitled "Nitro Group Terminated Mesogenic Epoxy Resin Adducts".

Copending Application Serial No. 07/832,070 (Atty. Docket No. C–39,899) filed Feb. 6, 1992 entitled "Mesogenic Cyclic Imino Ether–Containing Compositions and Polymerization Products Thereof".

Copending Application Serial No. 08/119,852 (Atty. Docket No. C–39,899–A) filed Sep. 10, 1993 entitled "Mesogenic Cyclic Imino Ether–Containing Compositions and Polymerization Products Thereof".

Copending Application Serial No. 08/107,267 (Atty. Docket No. C–38,979–C) filed Aug. 16, 1993 entitled "Thermoplastic Resins From Polyglycidyl Esters Containing Mesogenic Moieties".

(List continued on next page.)

*Primary Examiner*—Werren B. Lone

[57] ABSTRACT

4,4'-Dihydroxy-alpha-alkylstilbenes of high purity are prepared by reacting at a temperature of from about −20° C. to about 20° C. a mixture of (1) at least one alpha-haloketone, (2) at least one phenolic hydroxyl-containing compound or alkoxy-containing aromatic compound, and (3) at least one strong protonic acid or Lewis acid; such that the mole ratio of phenolic hydroxyl-containing compound or alkoxy-containing aromatic compound:alpha-haloketone(s) is from 0.1:1 to 1.9:1, and the mole ratio of phenolic hydroxyl-containing compound or alkoxy-containing aromatic compound:alpha-haloketone(s):strong protonic acid or Lewis acid is from about 0.1:1:0.0026 to about 1.9:1:0.95. The high purity 4,4'-dihydroxy-alpha-alkylstilbenes are useful for the advancement of epoxy resins, for the preparation of phenoxy resins and for the preparation of epoxy resins.

11 Claims, No Drawings

OTHER PUBLICATIONS

Copending Application Serial No. 08/107,409 (Atty. Docket No. C–38,979–D) filed Aug. 16, 1993 entitled "Mesogenic Glycidyl Esters".

Copending Application Serial No. 08/097,346 (Atty. Docket No. C–38,057–C) filed Jul. 23, 1993 entitled "Diamino–Aplha–Alkylstilbenes".

Copending Application Serial No. 08/118,485 (Atty. Docket No. C–38,057–D) filed Sep. 8, 1993, entitled "Adducts of Epoxy Resins and Active Hydrogen Containing Compounds Containing Mesogenic Moieties".

Copending Application Serial No. 07/562,289 (Atty. Docket No. C–38,057) filed Aug. 3, 1990 entitled "Sulfonamide Compounds Containing Mesogenic Moieties".

Copending Application Serial No. 07/746,527 (Atty. Docket No. C–37,610–A) filed Aug. 16, 1991 entitled "Mesogenic Polycyanates and Thermosets Thereof".

Copending Application Serial No. 08/091,459 (Atty. Docket No. C–37,610–D) filed Jul. 13, 1993 entitled "Mesogenic Polycyanates and Thermosets Thereof".

Copending Application Serial No. 08/091,460 (Atty. Docket No. C–37, 610–E) filed Jul. 13, 1993 entitled "Mesogenic Polycyanates and Thermosets Thereof".

Copending application Serial No. 08/091,150 (Atty. Docket No. C–37,610–F) filed Jul. 13, 1993 entitled "Mesogenic Polycyanates and Thermosets".

Journal of Polymer Science, Polymer Chemistry Edition, vol. 26, No. 8, 5 Aug. 1988 New York pp. 2047–2076, V Percec, et al., "Synthesis and characterisation of liquid crystalline copolymethacrylates, copolyacrylates, and copolysiloxanes containing 4–methoxy–4–hydroxy–alpha–methylstilbene and 4–hydroxy–4–methoxy–alpha–methylstilbene constitutional isomers as side–groups".

Journal of Polymer Science, Polymer Chemistry Edition, vol. 25, No. 7, July 1987, New York, pp. 1943–1965, V Percer, et al., "Functional polymers and sequential copolymers by phase transfer catalysis. 24. The influence of molecular weight on the thermotropic properties of a random copolyether based on 1,5–dibromopentane, 1,7–dibromoheptane, and 4,4 dihydroxy–alpha–methylstilbene".

PREPARATION OF 4,4'-DIHYDROXY-ALPHA'-DIALKYLSTILBENES AND 4, 4'-DIHYDROXY-ALPHA'-DIALKYLSTILBENES

CROSS-REFERENCE TO RELATED APPLICATION

This application is a division of application Ser. No. 08/162,517 filed Dec. 3, 1993, now U.S. Pat. No. 5,414,510, which is incorporated herein by reference in its entirety.

FIELD OF THE INVENTION

The present invention concerns a process for the production of 4,4'-dihydroxy-alpha-alkylstilbenes of high purity as well as the 4,4'-dihydroxy-alpha-alkylstilbene compositions resulting from said process.

BACKGROUND OF THE INVENTION

Preparation of 4,4'-dihydroxy-alpha-methylstilbene is delineated in an article entitled "Reactions of alpha-Halogeno-ketones with Aromatic Compounds. Part I. Reactions of Chloroacetone and 3-Chlorobutanone with Phenol and its Ethers" by S. H. Zaheer, et al., *Journal Of the Chemical Society*, Part 3, pages 3360–3362 (1954). In a typical synthesis, concentrated sulfuric acid was added to a mixture of phenol and chloroacetone in a 2:1 mole ratio followed by workup to provide 4,4'-dihydroxy-alpha-methylstilbene. In a similar synthesis, substitution of 3-chlorobutan-2-one for the chloroacetone provided 2,3-di-p-hydroxyphenylbut-2-ene. The 4,4'-dihydroxy-alpha-methylstilbene produced via the method of Zaheer, et al. as obtained from workup was very impure, as was shown by the low melting point of 115°–20° C. A pair of recrystallizations from alcohol were required to raise the melting point to 176°–179° C, and even after a third recrystallization from benzene, the melting point was only 182°–183° C.

Preparation of 4,4'-dihydroxy-alpha-methylstilbene is delineated in an article entitled "Synthesis and Characterization of Thermotropic Polyethers and Copolyethers Based on 4,4'-Dihydroxy-alpha-methylstilbene and Flexible Spacers Containing Odd Numbers of Methylene Units" by V. Percec, et al., *Mol. Cryst. Liq. Cryst.*, volume 205, pages 47–66 (1991). In the synthesis, concentrated sulfuric acid was added to a mixture of phenol and chloroacetone at −10 to −15 deg. C to provide a 2.0:0.995:0.47 mole ratio of phenol:chloroacetone:sulfuric acid. Workup of the precipitated product required six recrystallizations from ethanol/water (6/4 vol./vol.) and provided a 5.9 percent yield of 4,4'-dihydroxy-alpha-methylstilbene with a purity of 99.6–99.9 percent by high pressure liquid chromatographic analysis and a melting point of 185 deg. C. by differential scanning calorimetry at 20 deg. C. per minute.

Processes for the reaction of ketones with phenols to provide bisphenols typically depend upon the use of a substantial excess of phenol to ketone stoichiometry to minimize coproduct formation and provide a product with reasonable purity. As an example, G. F. Dugan and A. H. Widiger, Jr., U.S. Pat. No. 3,326,986 (1967), reacted a mixture of phenol and acetone in a 2.1:1 mole ratio in the presence of aqueous hydrochloric acid, o-dichlorobenzene solvent, n-octylmercaptan promoter and a stream of anhydrous hydrochloric acid sparged into the reaction mixture to provide bisphenol A (4,4'-isopropylidenediphenol). The coproducts produced in this reaction are extracted by multiple washing steps with chloroform. As a second example, J. I. de Jong, British Patent No. 949,668 (1964), combined a solution of phenol in toluene with sulfuric acid and thioglycolic acid promoter followed by addition of acetone. The mole ratio of phenol to acetone used was 2.1:1. After dilution with water, heating to provide a solution, washing with water, then adjustment of pH, bisphenol A crystallizes from the mixture leaving coproducts behind in the toluene mother liquor and aqueous layer. As a third example, W. C. Stoesser and E. H. Sommerfield, U.S. Pat. No. 2,623,908 (1952), developed a process for bisphenol A (4,4'-isopropylidenediphenol) wherein phenol and acetone in a 7.47:1 mole ratio were condensed in the presence of hydrogen chloride to provide a crystalline adduct of phenol and bisphenol A from which bisphenol A of high purity was recovered. As a fourth example, A. R. Grover and R. E. Richardson, U.S. Pat. No. 3,221,061 (1965), feed a continuous reactor zone containing a fixed bed of catalyst (sulfonated ion exchange resin promoted with mercaptoethanol) with a mixture rich in phenol with respect to acetone, for example, 84.7% phenol, 4.5% acetone, 0.1% water, 6.4% bisphenol A and 4.3% by-products, as a part of a process to produce bisphenol A. As a fifth example, K. H. Meyer and H. Schnell, German Patent No. 1,031,788 (1958), reacted a mixture of phenol and cyclohexanone in a 5.38:1 mole ratio in the presence of aqueous hydrochloric acid to provide crystalline adduct of phenol and bisphenol C (1,1-bis(4-hydroxyphenyl)cyclohexane) from which bisphenol C was recovered. As a sixth example, A. G. Farnham and F. P. Klosek, U.S. Pat. No. 2,812,364 (1957), combined phenol, aqueous hydrochloric acid and water to which formalin solution was added. A residue was obtained upon workup which provided bis(4-hydroxyphenyl)methane upon dissolution in hot aqueous acetic acid followed by cooling. The mole ratio of phenol to formaldehyde used was 5.9:1.

All of the reactions of phenol and chloroacetone with an acid reported in the Zaheer, et al. article were performed at a reaction scale well below one mole of phenol. In the Percec, et al. article, the reaction was performed using a mole ratio of phenol:chloroacetone:sulfuric acid of 1.26:0.627:0.296, which is less sulfuric acid stoichiometry than needed to fully react all of the phenol and chloroacetone present. In the hands of the present inventors, attempts to use the reaction methods of Zaheer, et al. at their stoichiometric ratios of 2:1:1 phenol:chtoroacetone:sulfuric acid at a reaction scale using one or greater moles of phenol invariably induced the formation of a highly viscous reaction mixture at the latter stages of the reaction followed by an exothermic decomposition of the reaction product. Thus as an improvement upon the method of Zaheer, et al., the present inventors discovered that a solvent, e.g. methylene chloride, could be used to moderate reaction viscosity and thus allow for heat transfer required for scaleups based on a reaction scale of one or more moles of phenol. This use of the solvent is indicated in the Comparative Experiments provided herein. Also, the present inventors evaluated, as indicated in the Comparative Experiments provided herein, the typically aforementioned use of a substantial excess of phenol to ketone stoichiometry in bisphenol synthesis to attempt to minimize coproduct formation and provide a product with reasonable purity.

While the use of a solvent and the adaptation of the excess phenol to chloroacetone stoichiometry provided the present inventors with 4,4'-dihydroxy-alpha-methylstilbene of acceptable purity for numerous end uses such as, for example, preparation of epoxy resins, the need exists for 4,4'-dihydroxy-alpha-methylstilbene of still higher purity for such uses as linear advancement of epoxy resins. It was recognized that purity improvements meant not only reduction of coproduct levels obtained in the current process, but also elimination of coproducts wherever possible. Furthermore, the need exists to simplify the process for producing 4,4'-dihydroxy-alpha-methylstilbene by eliminating the need for an additional chemical, the solvent such as methylene chloride, used in the process and its subsequent removal. Additionally, obtaining isolated 4,4'-dihydroxy-alpha-methylstilbene yields above the relatively modest yields provided by the current processing methods was deemed to be desirable.

In the present invention it was surprisingly found that the use of alpha-haloketone in the synthesis of 4,4'-dihydroxy-alpha-alkylstilbenes using phenol or alkoxybenzene:alpha-haloketone mole ratios of less than 2:1 provides one or more of the aforementioned improvements such as increased product purity, elimination of the need for solvent, or increase in isolated product yield.

SUMMARY OF THE INVENTION

One aspect of the present invention pertains to a process for preparing 4,4'-dihydroxy-alpha-alkylstilbenes or 4,4'-dihydroxy-alpha, alpha'-dialkylstilbenes, said process comprising (A) reacting at a temperature of from about −20° C. to about 20° C. a mixture of
  (1) at least one alpha-haloketone;
  (2) at least one compound containing one phenolic hydroxyl group per molecule such that the mole ratio of phenolic hydroxyl group-containing compound(s):alpha-haloketone(s) is from 0.1:1 to 1.9:1; and
  (3) either (a) at least one strong protonic acid or (b) at least one Lewis acid, or (c) any combination thereof;
  such that the mole ratio of phenolic hydroxyl group-containing compound(s):alpha-haloketone(s):strong protonic acid or Lewis acid or combination thereof is from about 0.1:1:0.0026 to about 1.9:1:0.95;

(B) substantially removing or neutralizing any residual acidic materials from the product resulting from step (A); and (C) dehydrohalogenating the product retained from step (B).

Another aspect of the present invention pertains to a process which provides 4,4'-dihydroxy-alpha-alkylstilbenes or 4,4'-dihydroxy-alpha,alpha'-dialkylstilbenes, said process comprising (A) reacting at a temperature of from about 20° C. to about −20° C. a mixture of
  (1) at least one alpha-haloketone;
  (2) at least one aromatic compound containing one alkoxy group per molecule such that the mole ratio of alkoxy group-containing aromatic compound(s):alpha-haloketone(s) is from 0.1:1 to 1.9:1; and
  (3) either (a) at least one strong protonic acid or (b) at least one Lewis acid, or (c) any combination thereof;
  such that the mole ratio of alkoxy group-containing aromatic compound(s):alpha-haloketone(s):strong protonic acid or Lewis acid or combination thereof is from about 0.1:1:0.0026 to about 1.9:1:0.95;

(B) substantially removing or neutralizing any residual acidic materials from the product from step (A) of the aforementioned process employing compound(s) containing at least one alkoxy group per molecule;

(C) dehydrohalogenating the product retained from step (B); and

D) dealkylating the product resulting from step (C).

Another aspect of the present invention pertains to recovering the desired 4,4'-dihydroxy-alpha-alkylstilbene and/or 4,4'-dihydroxy-alpha,alpha'-dialkylstilbene product from the product resulting from either of the aforementioned processes.

A still further aspect of the present invention pertains to 4,4'-dihydroxy-alpha-methylstilbene having a melting point of at least 186° C., preferably at least 187° C., more preferably at least 188° C.

The aforementioned aspects of the invention can comprise, consist essentially of or consist of the various components employed in the process or composition.

DETAILED DESCRIPTION OF THE INVENTION

DEFINITIONS

The term "4,4'-dihydroxy-alpha-alkylstilbene(s)" is intended to encompass the 4,4'-dihydroxy-alpha, alpha'-dialkylstilbene(s), as well as the 4,4'-dihydroxy-alpha-alkylstilbene(s), per se in general discussions herein.

The term "hydrocarbyl" as employed herein means any aliphatic, cycloaliphatic, aromatic, aryl substituted aliphatic, aryl substituted cycloaliphatic, aliphatic substituted aromatic, or cycloaliphatic substituted aromatic groups. The aliphatic or cycloaliphatic groups can be saturated or unsaturated. Likewise the term "hydrocarbyloxy" means a hydrocarbyl group having an oxygen linkage between it and the carbon atom to which it is attached.

The term "strong protonic acid" as employed herein means a proton donor (Brönsted acid) which on a thermodynamic acidity scale possesses a pKa value relative to water of −0.5 or less, preferably −6 or less.

The term "Lewis acid" as employed herein means a substance which is an electron-pair acceptor, that is, a substance with a vacant orbital.

By the term "higher purity", it is meant that the process produces less coproducts and/or the resulting product possesses a higher melting point than the product produced using other known processes.

NUMERICAL VALUES

Any numerical values expressed herein include all values from the lower value to the upper value in increments of one unit provided that there is a separation of at least 2 units between any lower value and any higher value. As an example, if it is stated that the amount of a component is, for example, from 1 to 90, preferably 20 to 80, more preferably from 30 to 70, it is intended that values such as 15–85, 22–68, 43–51, 30–32 etc. are expressly enumerated in this specification. For values which are less than one, one unit is considered to be 0.1; therefore, the minimum separation between any lower value and any higher value is 0.2. These are only examples of what is specifically intended and all numerical values are to be considered to be expressly stated in this specification in a similar manner.

PHENOLIC HYDROXYL-CONTAINING COMPOUND(S)

Suitable phenolic hydroxyl-containing compounds which can be employed herein include most any monohydric phenol or phenolic compound lo represented by the following Formula I

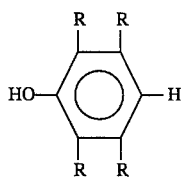

Formula I wherein each R is independently hydrogen or a hydrocarbyl or hydrocarbyloxy group having from 1 to about 12, preferably 1 to about 6, most preferably 1 to about 4, carbon atoms, a halogen atom, preferably chlorine, bromine or fluorine, a nitro group, a nitrile group, or a —CO—$R^1$ group; $R^1$ is hydrogen or a hydrocarbyl group having from 1 to about 8, preferably from 1 to about 4, most preferably from 1 to about 2, carbon atoms.

Particularly suitable phenolic hydroxyl-containing compounds which can be employed herein to prepare the 4,4'-dihydroxy-alpha-alkylstilbene(s) include, for example, phenol, 2,6-dimethylphenol, 2,6-diethylphenol, 2,6-dibromophenol, 2,6-dichlorophenol, 2,6-difluorophenol, 2,6-dimethoxyphenol, 2,6-diethylphenol, 3,5-dimethylphenol, 2-nitrophenol, 2-cyanophenol, 2-methylphenol, 3-methylphenol, 2-phenylphenol, 2-cyclohexylphenol, 2-octylphenol, 2-methyl-6-chlorophenol, 2-methoxy-6-chlorophenol, 2,3,5,6-tetramethylphenol, or any combination thereof and the like. Phenol is most preferred as the phenolic hydroxyl-containing compound.

ALKOXY GROUP-CONTAINING AROMATIC COMPOUND(S)

Suitable alkoxy group-containing aromatic compound(s) which can be employed herein include those compounds represented by the following Formula II

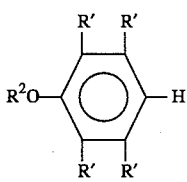

Formula II wherein each R' is independently hydrogen or a hydrocarbyl group having from 1 to about 12, preferably 1 to about 6, most preferably 1 to about 4, carbon atoms, a halogen atom, preferably chlorine, bromine or fluorine, a nitro group, a nitrile group, or a —CO—$R^1$ group; $R^1$ is hydrogen or a hydrocarbyl group having from 1 to about 8, preferably from 1 to about 4, most preferably from 1 to about 2, carbon atoms; and $R^2$ is a hydrocarbyl group having from 1 to about 12, preferably 1 to about 2, most preferably 1, carbon atoms.

Particularly suitable alkoxy group-containing aromatic compound(s) which can be employed herein to prepare the 4,4'-dihydroxy-alpha-alkylstilbenes include, for example, anisole, phenetole, 2,6-dimethylanisole, 2,6-diethylanisole, 2,6-dibromoanisole, 2,6-dichloroanisole, 2,6-difluoroanisole, 3,5-dimethylanisole, 2-nitroanisole, 2-cyanoanisole, 2-methylanisole, 3-methylanisole, 2-phenylanisole, 2-cyclohexylanisole, 2-octylanisole, 2-methyl-6-chloroanisole, 2-methoxy-6-chloroanisole, 2,3,5,6-tetramethylanisole, or any combination thereof and the like. Anisole (methoxybenzene) is most preferred as the alkoxy group-containing aromatic compound.

ALPHA-HALOKETONES

Suitable alpha-haloketones which can be employed herein include, most any alpha-haloketone, such as, for example, those represented by the following Formula III

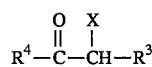

Formula III wherein $R^3$ is hydrogen or a hydrocarbyl group having from 1 to about 8, preferably 1 to about 4, most preferably 1 to about 2, carbon atoms; $R^4$ is a hydrocarbyl group having from 1 to about 8, preferably 1 to about 4, most preferably 1 carbon atoms; and X is a halogen atom, preferably chlorine or bromine.

When $R^3$ is other than hydrogen, the product produced will be a 4,4'-dihydroxy-alpha,alpha'-dialkylstilbene.

Particularly suitable alpha-haloketones which can be employed herein to prepare the 4,4'-dihydroxy-alpha-alkylstilbenes include, for example, chloroacetone, bromoacetone, 4-methyl-1-chloropentan-2-one, 1-chlorooctan-2-one, or any combination thereof and the like. Chloroacetone is most preferred as the alpha-haloketone for preparing the dihydroxy-alpha-alkylstilbenes.

Particularly suitable alpha-haloketones which can be employed herein to prepare the 4,4'-dihydroxy-alpha,alpha'-dialkylstilbenes include, for example, 3-chlorobutan-2-one, 2-chloropentan-3-one, 3-chloropentan-2-one, 4-methyl-3-chloropentan-2-one, 4-methyl-2-chloropentan-3-one, or any combination thereof and the like. 3-chlorobutan-2-one is most preferred as the alpha-haloketone for preparing the 4,4'-dihydroxy-alpha,alpha'-dialkylstilbenes.

The phenolic hydroxyl-containing compound(s) or alkoxy group-containing aromatic compound(s) and the alpha-haloketone(s) are employed in an amount such that the mole ratio of the phenol or alkoxy group-containing aromatic compound:alpha-haloketone is from about 0.1:1 to about 1.9:1, preferably from about 0.5:1 to about 1.85:1, most preferably from about 1:1 to about 1.80:1 When the ratio of phenol:alpha-haloketone is greater than 1.9:1, 4,4'-dihydroxy-alpha-alkylstilbenes or 4,4'-dihydroxy-alpha,alpha'-dialkytstilbenes of substantially reduced purity are produced as the dimeric coproduct content is increased. Furthermore, the viscosity of the reaction mixture is increased, making the removal of heat from the reaction more difficult. When the ratio of phenol:alpha-haloketone is less than 0.1:1, excessive dilution of the reaction by alpha-haloketone occurs with an increase in the amount of unreacted alpha-haloketone which has to be removed at the end of the reaction.

STRONG PROTONIC ACIDS

Suitable strong protonic acids which can be employed herein include, for example, sulfuric acid, sulfuric acid containing sulfur trioxide, sulfonic acid form of a cation ion exchange resin such as, for example, lo polystyrene lightly crosslinked with divinylbenzene, methanesulfonic acid, p-toluenesulfonic acid, hydrogen chloride, or any combination thereof and the like. Concentrated sulfuric acid is most preferred as the strong protonic acid.

LEWIS ACIDS

Suitable Lewis acids which can be employed herein include, for example, anhydrous aluminum chloride, tin tetrachloride, boron trifluoride, zinc chloride, boron trifluoride etherate, any combination thereof and the like. Anhydrous aluminum chloride is most preferred as the Lewis acid.

Combinations of strong protonic acids and Lewis acids can also be employed. These can be added sequentially, simultaneously or as preformed reaction products. $FSO_3H$-$SbF_5$ is an example of said preformed reaction products.

The strong protonic acid or Lewis acid is employed in an amount such that the mole ratio of phenolic hydroxyl-containing compound(s) or alkoxy group-containing aromatic compound(s):alpha-haloketone(s):strong protonic acid or Lewis acid is from about 0.1:1:0.0026 to about 1.9:1:0.95 preferably from about 0.5:1:0.020 to about 1.85:1:0.617, most preferably from about 1:1:0.1 to about 1.80:1:0.225.

When the ratio of phenolic hydroxyl-containing compound(s) or alkoxy group-containing aromatic compound(s):strong protonic acid(s) or Lewis acid(s) is greater than 2:1 within the aforementioned mole ratios given for the phenolic hydroxyl-containing compound(s) or alkoxy group-containing aromatic compound(s):alpha-haloketone(s):strong protonic acid or Lewis acid, a stoichiometric deficiency of acid exists and results in incomplete conversion of the phenolic hydroxyl-containing compound(s) or alkoxy group-containing aromatic compound(s) to the desired 4,4'-dihydroxy-alpha-alkylstilbene product. The resultant unreacted phenolic hydroxyl-containing compound(s) or alkoxy group-containing aromatic compound(s) must be removed at the end of the reaction and can then be recovered and eventually recycled.

When the ratio of phenolic hydroxyl-containing compound(s) or alkoxy group-containing aromatic compound(s):strong protonic acid or Lewis acid is less than 2:1 within the aforementioned mole ratios given for the phenolic hydroxyl-containing compound(s) or alkoxy group-containing aromatic compound(s):alpha-haloketone(s):strong protonic acid or Lewis acid, a stoichiometric excess of acid is present and can accelerate the conversion of reactants not only ultimately to the desired 4,4'-dihydroxy-alpha-alkylstilbene product, but also to coproducts, such as those formed from the acid catalyzed dimerization of the 4,4'-dihydroxy-alpha-alkylstilbene.

In the process of the present invention, the phenolic hydroxyl-containing compound(s) or alkoxy group-containing aromatic compound(s) and the alpha-haloketone(s) are combined together then chilled to about −20° C. to about +20° C., preferably to about −15° C. to about +10° C., most preferably to about −13° C. to about 0° C. The strong protonic acid or Lewis acid is then added to the mixture of the phenol or phenol equivalent and the alpha-haloketone at such a rate as to maintain the aforementioned temperatures for the reaction. The time required to complete the addition of the strong protonic acid or Lewis acid depends upon the reaction temperature, reactants employed, the heat transfer ability of the reactor employed and other such variables. Higher temperatures require shorter periods of time whereas longer temperatures require longer periods of time. Generally, however, times of from about 5 minutes to about 12 hours, preferably from about 15 minutes to about 8 hours, most preferably from about 30 minutes to about 4 hours are suitable. The reaction can be conducted at atmospheric, superatmospheric or subatmospheric pressures. The time required to complete the reaction depends upon the addition time of the strong protonic acid or Lewis acid, the reaction temperature, the heat transfer ability of the reactor employed and other such variables. Higher temperatures require shorter periods of time whereas lower temperatures require longer periods of time. Generally, however, times of from about 5 minutes to about 24 hours, preferably from about 2 hours to about 20 hours, most preferably from about 4 hours to about 18 hours are suitable. The reaction can be performed as a batch process or continuous process. It is frequently of benefit to conduct the reaction under an inert atmosphere, such as nitrogen, especially if the particular equipment used can entrain air which contains moisture.

In the process of the present invention, it is typically desirable to chose a reaction time and temperature profile which provides the greatest conversion and selectivity to the tertiary chloride precursor and subsequently to the 4,4'-dihydroxy-alpha-alkylstilbene product. For the reaction employing phenol and chloroacetone as reactants, the tertiary chloride, 1,2-(4-hydroxyphenyl)-2-chloropropane, is the precursor to the 4,4'-dihydroxy-alpha-methylstilbene product. Thus, for example, subjecting phenol, chloroacetone and sulfuric acid to higher temperatures for prolonged periods of time, favors the formation of undesirable 1,2,2-tris( 4-hydroxyphenyl)propane, presumably via reaction of intermediate 1,2-(4-hydroxyphenyl)-2-chloropropane with phenol. This effectively lowers the amount of 1,2-(4-hydroxyphenyl)-2-chloropropane available for thermally induced dehydrochlorination to the desired 4,4'-dihydroxy-alpha-methylstilbene product. Higher reaction temperatures coupled with longer reaction times also favor the ultimate formation of undesirable dimeric species in the 4,4'-dihydroxy-alpha-methylstilbene product as does reaction stoichiometry leading to an excess of acid with respect to the phenolic hydroxyl-containing compound(s) or alkoxy group-containing aromatic compound(s)employed (mole ratios of less than 2:1 phenolic hydroxyl-containing compound(s) or alkoxy group-containing aromatic compound(s):strong protonic acid or Lewis acid). The structures postulated for these undesirable dimeric species which arise as a result of acid catalyzed dimerization of 4,4'-dihydroxy-alpha-methylstilbene are given as follows:

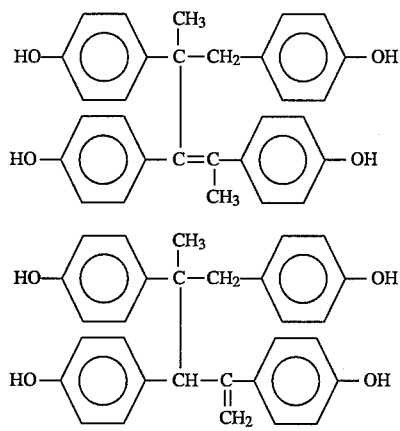

Thus, it is frequently of value to conduct simple preliminary experiments over the range of reaction variables which can be employed in order to define an optimum reaction time and temperature profile which provides the greatest conversion and selectivity for the tertiary chloride precursor to the 4,4'-dihydroxy-alpha-alkylstilbene product. In this manner, conditions not conducive to optimizing the yield of high purity 4,4'-dihydroxy-alpha-alkylstilbene can be avoided.

ACID REMOVAL OR NEUTRALIZATION STEP

Removal or neutralization of the strong protonic acid or Lewis acid and/or the products resulting from reaction of said acids during the reaction is accomplished using any unit operations which will effectively remove the acid such as washing with water, buffering, neutralization over a suitable ion exchange resin, neutralization with a basic acting substance, such as, for example, alkali metal carbonates, bicarbonates or hydroxides such as, for example sodium bicarbonate, potassium bicarbonate, sodium hydroxide, any combination thereof and the like. When a Lewis acid such as anhydrous aluminum chloride is employed, initial neutralization with cold dilute hydrochloric acid is used as the initial step in the removal. It is also suitable to utilize combinations of unit operations which will effectively neutralize the acid in the reaction product, such as initially washing with water, followed by washing with an aqueous solution of a basic acting substance. Likewise, the equipment associated with the aforementioned unit operations is chosen to maximize processability. Thus, for example, a centrifuge can be used to rapidly separate aqueous and organic layers resulting from the washing. A static coalescer can be used to induce rapid resolution of emulsified aqueous and organic layers resulting from the washing. In the case of the reaction crude prepared from phenol and chloroacetone, if the unit operations employed to remove the acid lead to an increase in temperature, especially above 10° C., then substantial dehydrohalogenation of the tertiary chloride intermediate to the 4,4'-dihydroxy-alpha-alkylstilbene product can also occur.

When the acid content is reduced or eliminated by neutralization with a basic acting substance, the basic acting substance is usually employed in a stoichiometric or slightly less than the stoichiometric amount required to theoretically neutralize the desired proportion of the acid content.

The acid removal or neutralization step reduces the amount of strong protonic acids or Lewis acids or combination thereof and/or the products resulting from said acids in the reaction product to an amount from about 10,000 ppm to 0 ppm, preferably from about 1,000 ppm to 0 ppm, more preferably from about 250 ppm to 0 ppm.

This acid removal or neutralization step of the process can be conducted at temperatures of from about $-20°$ C. to about 75° C., preferably from about $-5°$ C. to about 50° C., more preferably from about 0° C. to about 10° C.

At temperatures below about $-20°$ C., acid removal or neutralization can be hindered by freezing out of water if used for washing or as a solvent for the buffer or basic acting substance. Temperatures below $-20°$ C. also favor the formation and stabilization of emulsions, such as are formed in the washing process, thus making resolution of acid from the reaction product difficult.

At temperatures above about 75° C., substantial dehydrohalogenation of the tertiary chloride intermediate to the 4,4'-dihydroxy-alpha-methylstilbene product can induce premature precipitation of said product. Additionally, the higher temperatures can favor the formation of coproducts, such as trisphenol formed via reaction of tertiary chloride intermediate with phenol, especially if the acid removal or neutralization process employed does not rapidly dilute the acid present in the reaction product.

DEHYDROHALOGENATION STEP

The dehydrohalogenation of the tertiary chloride precursor to the 4,4'-dihydroxy-alpha-alkylstilbene product is generally accomplished by heating of the washed reaction crude product from the acid removal step to a temperature of at least about 60° C. to about 125° C., preferably about 70° C. to about 90° C., most preferably 75° C. to about 85° C. Once the desired temperature is achieved, it is maintained until completion of the thermal is dehydohalogenation, typically for from about one second to about two hours, preferably from about ten seconds to about 30 minutes, most preferably from about 30 seconds to about 5 minutes. It is frequently desirable to monitor the course of the thermal dehydrohalogenation via an analytical method, such as high pressure liquid chromatographic analysis. Additionally, it is frequently of value to conduct simple preliminary experiments over the range of reaction variables which can be employed in order to define an optimum reaction time and temperature profile which provides the greatest conversion and selectivity for the tertiary chloride precursor to the 4,4'-dihydroxy-alpha-alkylstilbene product from the thermal dehydrohalogenation step. In this manner, conditions not conducive to optimizing the yield of high purity 4,4'-dihydroxy-alpha-alkylstilbene, can be avoided. It is frequently of benefit to add water to the washed reaction crude prior to the thermal dehydrohalogenation. This water serves to dilute any hydrogen halide released during the thermal dehydrohalogenation and not volatilized out of the product and additionally dilutes any traces of acid incompletely removed from the reaction crude by the prior acid removal process, such as water washing. The amount of water varies depending upon the amount of water retained in the washed reaction crude, the amount of residual acid present in the washed reaction crude, the amount of acid expected to be liberated from the thermal dehydrohalogenation, and other such variables, but typically is used in an amount of from about 5 to about 70, preferably from about 10 to about 50, most preferably from about 20 to about 35 percent by weight of the combined weight of the reaction crude and water used. The water can also contain a neutralization agent, such as the aforementioned basic acting substance, however, care must be taken that the amount of neutralization agent is not in an amount that causes the thermal dehydrohalogenation reaction to be basic during the entire course of said reaction. During the thermal dehydrohalogenation, stirring or mixing is desirable to assure even heating of the reaction crude and complete dispersion of the water, if added. During the course of the thermal dehydrohalogenation, excess chloroacetone can be distilled from the mixture and recovered for further use. This distillation can be assisted by the application of a vacuum during the thermal dehydrohalogenation step. Once the thermal dehydrohalogenation is complete, water is added to the stirred or mixed reaction product. This serves to quench the thermal dehydrohalogenation reaction by cooling and dilution of the reaction mixture, as well as to force precipitation of the crystalline 4,4'-dihydroxy-alpha-alkylstilbene product. The amount of water used varies depending upon the structure of the particular 4,4'-dihydroxy-alpha-alkylstilbene formed; the structure and amount of the reactants employed, especially the phenol or alkoxy group-containing aromatic compound; the amount of water used in the thermal dehydrohalogenation step; the amount of water retained in the washed reaction crude; and other such variables, but typically is used in an amount from about 125 to about 10, preferably from about 100 to about 30 most preferably from about 40 to about 80 percent by weight of the combined weight of the reaction crude and water used. If desired, crystallization of the mixture of the thermal dehydrohalogenation product and water can be induced or accelerated via the addition of seed crystals of the particular 4,4'-dihydroxy-alpha-alkylstilbene product being prepared, however this is typically unnecessary. It is frequently of value to conduct simple preliminary experiments over the range of time and temperature at which the crystalline slurry can be held in order to define an optimum time and temperature profile which provides the greatest isolated yield of the 4,4'-dihydroxy-alpha-alkylstilbene product. Typically, the crystalline slurry is held-at temperatures of from about 0° C. to about 60° C., preferably from about 4° C. to about 40° C., most preferably from about 4° C. to about 25° C. and for times from about 10 minutes to about one week, preferably from about one hour to about 48 hours, most preferably from about 8 hours to about 24 hours. The product is recovered from the crystalline slurry using any unit operations which effectively remove the crystals from said slurry, such as, for example, filtration or centrifugation. The recovered product can be dried, for example in an oven under vacuum, or utilized as recovered as a wet cake.

DEALKYLATION STEP

When an alkoxy group-containing aromatic compound, such as anisole, is utilized in the process of the present invention, the resulting 4,4'-dialkoxy-alpha-alkylstilbene can be converted to the corresponding 4,4'-dihydroxy-alpha-alkylstilbene using methods well established in the prior art. Such methods include, for example, (A) heating of the 4,4'-dialkoxy-alpha-alkylstilbene to reflux for ten hours in 2,4,6-trimethylpyridine containing lithium iodide in the manner taught by I. T. Harrison, *Journal of Organic Chemistry*, 28, 2184 (1963); or (B) addition of the 4,4'-dialkoxy-alpha-alkylstilbene (may be as a solvent solution, for example, in methylene chloride, benzene, pentane, hexane) to boron tribromide (may be in solvent, for example, in methylene chloride, benzene, pentane, hexane) under a dry atmosphere, followed by reaction at 20° to 25° C. for 12 to 16 hours in the manner taught by J. F. W. McOmie, M. L. Watts and D. E. West, *Tetrahedron*, 24, 2289 (1968); or (C) refluxing of the 4,4'-dialkoxy-alpha-alkylstilbene in 48% hydrobromic acid in acetic acid for at least thirty minutes in the manner taught by I. Kawasaki, K. Matsuda and T. Kaneko, *Bulletin of the Chemical Society of Japan*, 44, 1986 (1971). All of the aforementioned citations are incorporated herein by reference in their entirety.

PRODUCT RECOVERY STEP

The resultant 4,4'-dihydroxy-alpha-alkylstilbene product can be further processed for the purpose of upgrading or otherwise modifying product purity by any of the techniques well known to the skilled artisan. Such techniques include, for example, extraction by water and/or organic solvents, recrystallization from organic solvents, sublimation, zone refining, crystal refining, column chromatography, and the like or combinations thereof. A preferred method of post treatment is boiling water extraction of the 4,4'-dihydroxy-alpha-alkylstilbene product recovered as a wet cake from the dehydrohalogenation step. In this method, the 4,4'-dihydroxy-alpha-alkylstilbene product is slurried in water, brought to a boil and either filtered hot or cooled and then filtered.

When a phenolic hydroxyl-containing compound is employed the resultant 4,4'-dihydroxy-alpha-alkylstilbene compound is believed to be a compound represented by the following Formula IV

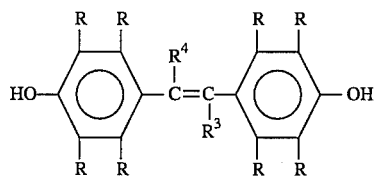

Formula IV wherein each R, $R^3$ and $R^4$ are as previously defined.

When an alkoxy group-containing aromatic compound is employed and the resultant 4,4'-dialkoxy-alpha-alkylstilbene is dealkylated, the resultant 4,4'-dihydroxy-alpha-alkylstilbene compound is believed to be a compound represented by the following Formula V

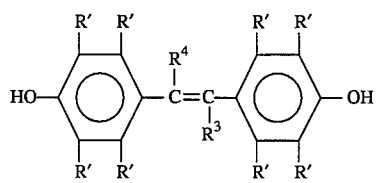

Formula V wherein each R', $R^3$ and $R^4$ are as previously defined.

The product actually produced is a mixture of cis and trans isomers with the trans isomer being predominant.

The product resulting from the present invention is a 4,4'-dihydroxy-alpha-alkylstilbene with higher purity and/or the product is recovered in higher isolated yield than that attainable using conventional processes for bisphenols. In the case of 4,4'-dihydroxy-alpha-methylstilbene, the higher purity results in a higher melting point product than that obtained in the prior art or that obtained by using processes of the prior art.

The high purity 4,4'-dihydroxy-alpha-alkylstilbene products of the present invention are useful for the advancement of epoxy resins, for the preparation of phenoxy resins and for the preparation of epoxy resins.

The following examples are exemplary of the invention but are not to be construed as to limiting the scope thereof in any manner.

The chloroacetone employed in each of the examples and comparative experiments is a commercial grade containing 96.5% chloroacetone, 3.0% 1,1-dichloroacetone, 0.40% mesityl oxide, 0.05% acetone and 0.05% high boiling compounds.

EXAMPLE 1

Synthesis of 4,4'-Dihdyroxy-alpha-methylstilbene Using a Phenol:Chloroacetone;Sulfuric Acid Mole Ratio of 1.805:1.0:0.1805

A. Reaction Step

Phenol (941 grams, 10.0 moles) and chloroacetone (531.6 grams, 5.54 moles as chloroacetone) are added to a 5 liter glass reactor equipped with a chilled water condenser, mechanical stirrer, nitrogen purge (one liter per minute), thermometer, dropping funnel and jacket for circulating coolant over the reactor exterior. The chloroacetone is employed in a 1.805:1 mole ratio of phenol:chloroacetone. Stirring commences concurrent with cooling of the reactant solution to −10° C. Concentrated sulfuric acid (98.2 grams, 1.0 mole) is added to the dropping funnel, then dropwise addition to the stirred reactant solution commences over a 40 minute period and so as to maintain the reaction temperature between −10° C. and −13° C. After 17 hours and 15 minutes of post reaction at −12° C., high pressure liquid chromatographic (HPLC) analysis of a portion of the product using a uv detector set at 254 nm reveals the presence of the following area percent distribution of components in their relative order of elution: phenolsulfonic acids—0.46, chloroacetone—1.32, phenol—64.05, 1,2,2-tris(4-hydroxyphenyl)propane—trace, 4,4'-dihydroxy-alpha-methylstilbene—21.69, 1,2-(4-hydroxyphenyl)-2-chloropropane—9.59, higher retention time compounds—1.26 plus 1.64.

B. Acid Removal Step

At this time, chilled (8° C.) deionized water (1000 milliliters) is added to the stirred reaction product inducing an exotherm to 0° C., then after two minutes of mixing, the opaque, pale pink colored product is recovered and divided equally into a pair of 2 liter glass separatory funnels. The contents of each separatory funnel are washed four times each with 500 milliliter portions of 45° C. deionized water. The combined organic layers are recovered and divided equally into a pair of 4 liter glass beakers.

C. Dehydrohalogenation Step

The contents of each beaker are stirred, deionized water (260 milliliters) is added and heating commences. Once a temperature of −80° C. is achieved, heating ceases and deionized water is added to each beaker in an amount sufficient to produce a total volume of 3.8 liters.

D. Product Recovery Step

The resultant crystalline slurry which forms is maintained with stirring for the next 16 hours at room temperature (23° C.). At this time, stirring is stopped and the crystalline product is recovered via filtration of the crystalline slurry, then added to a glass beaker and combined therein with deionized water (one liter). Stirring and heating commence until the stirred slurry reaches 100° C. After 5 minutes at 100° C., the stirred slurry is filtered through a fritted glass filter. The product recovered from the filter is dried in a vacuum oven at 80° C. and one mm Hg to a constant weight of 187.6 grams of pale pink colored crystalline product.

E. Results and Product Analysis

The yield of isolated product based on sulfuric acid stoichiometry employed is 83.0%. HPLC analysis of a portion of the product reveals the presence of the following area percent distribution of components in their relative order of elution: phenol—0.074, 4,4'-dihydroxy-alpha-methylstilbene—92.42, 4,4'-dihydroxy-alpha-methylstilbene dimer A—6.46, unknown at slightly higher retention time than dimer A—0.336, 4,4'-dihydroxy-alpha-methylstilbene dimer B plus dihydroxy-alpha-methylstilbene isomer—0.387. Since the aforementioned HPLC analytical method does not resolve 1,2,2-tris(4-hydroxyphenyl)propane from the 4,4'-dihydroxy-alpha-methylstilbene peak, a separate method of HPLC analysis is employed and reveals the presence of none of this trisphenol. Differential scanning calorimetry of portions of the product (12.1 and 31.7 milligrams) using a heating rate of 10° C./min. from 30° C. to 300° C. under a nitrogen atmosphere flowing at 35 cubic centimeters per minute reveals a single sharp melting point endotherm with a minimum at 188.4° C. and an enthalpy of 139.4 joules per gram (average of two samples). High pressure liquid chromatography-mass spectrometry confirmed the structure of 4,4'-dihydroxy-alpha-methylstilbene (m/e parent radical cation and base peak=226), 4,4'-dihydroxy-alpha-methylstilbene dimer A (m/e parent radical cation=452, m/e base peak=227), dihydroxy-alpha-methylstilbene isomer (m/e parent radical cation and base peak=226), 4,4'-dihydroxy-alpha-methylstilbene dimer B (m/e parent radical cation=452, m/e base peak=227). The dihydroxy-alpha-methylstilbene isomer and 4,4'-dihydroxy-alpha-methylstilbene dimer B peaks are not sufficiently resolved by the HPLC analysis for separate integration of each respective component. The high pressure liquid chromatography-mass spectrometry analysis was performed using a Finnigan SSQ-710 mass spectrometer interfaced to a Hewlett-Packard 1090M liquid chromatograph. A Keystone ODS column (250 mm by 4.6 mm) was used. The mobile phase gradient used was as follows with a flow set at 0.7 milliliters per minute: initial=30% acetonitrile, 70% water; 15 minutes=55% acetonitrile, 45% water; 20 minutes=70% acetonitrile, 30% water; 25 minutes=95% acetonitrile, 5 water; 27 minutes=30% acetonitrile and 70% water. The diode-array detector was set at 220 nm and the signal was sent to the mass spectrometer data system. After passing through the diode-array detector, o the liquid stream entered the mass spectrometer via a particle beam liquid chromatograph-mass spectrometer interface set at 60° C. Electron impact mass spectra of the eluted components were collected from 50 to 650 amu at 2 second intervals. The mass spectrometer source temperature was set at 250° C. Proton magnetic resonance spectroscopy and Fourier transform infrared spectrophotometric analysis additionally confirm the product structure.

EXAMPLE 2

A second synthesis is performed in a manner identical to that of Example 1 above and provides 190.2 grams of a pale pink colored product. The yield of isolated product based on sulfuric acid stoichiometry employed is 84.2%. Differential scanning calorimetry of portions of the product (6.6 and 8.3 milligrams) using a heating rate of 0° C./min. from 30° C. to 300° C. under a nitrogen atmosphere flowing at 35 cubic centimeters per minute reveals a single sharp melting point endotherm with a minimum at 189.0° C. and an enthalpy of 148.3 joules per gram (average of two samples).

EXAMPLE 3

Synthesis of 4,4'-Dihydroxy-alpha-methylstilbene using a Phenol:Chloroacetone:Sulfuric Acid Mole Ratio of 1.90:1.0:0.1901

A. Reaction Step

Phenol (941 grams, 10.0 moles) and chloroacetone (504.9 grams, 5.26 moles as chloroacetone) are added to a 5 liter glass reactor equipped with a chilled water condenser, mechanical stirrer, nitrogen purge (one liter per minute), thermometer, dropping funnel and jacket for circulating coolant over the reactor exterior. The chloroacetone is employed in a 1.901:1 mole ratio of phenol:chloroacetone. Stirring commences concurrent with cooling of the reactant solution to −10° C. Concentrated sulfuric acid (98.2 grams, 1.0 mole) is added to the dropping funnel, then dropwise addition to the stirred reactant solution commences over a 81 minute period and so as to maintain the reaction temperature between −10° C. and −12° C. After 17 hours and 35 minutes of post reaction at −12° C., high pressure liquid chromatographic (HPLC) analysis of a portion of the product using a uv detector set at 254 nm reveals the presence of the following area percent distribution of components in their relative order of elution: phenolsulfonic acids—0.07, chtoroacetone—1.39, phenol—72.61, 1,2,2-tris(4-hydroxyphenyl)propane—0.28, 4,4'-dihydroxy-alpha-methylstilbene—4.87, 1,2-(4-hydroxyphenyl)-2-chloropropane—19.16, higher retention time compounds—0.161 plus 0.833 plus 0.245.

B. Acid Removal Step

At this time, chilled (3° C.) deionized water (1000 milliliters) is added to the stirred reaction product inducing an exotherm to 0° C., then after two minutes of mixing, the opaque, pale pink colored product is recovered and divided equally into a pair of 2 liter glass separatory funnels.

C. Dehydrohalogenation Step

The contents of each separatory funnel are washed four times each with 500 milliliter,portions of 45° C. deionized water. The combined organic layers are recovered and divided equally into a pair of 4 liter glass beakers. The contents of each beaker are stirred, deionized water (260 milliliters) is added and heating commences. Once a temperature of 80° C. is achieved, heating ceases and deionized water is added to each beaker in an amount sufficient to produce a total volume of 3.8 liters.

D. Product Recovery Step

The resultant crystalline slurry which forms is maintained with stirring for the next 16 hours at room temperature (23° C.). At this time, stirring is stopped and the crystalline product is recovered via filtration of the crystalline slurry then added to a glass beaker and combined therein with deionized water (one liter). Stirring and heating commence until the stirred slurry reaches 100° C. After 5 minutes at 100° C., the stirred slurry is filtered through a fritted glass filter. The product recovered from the filter is dried in a vacuum oven at 80° C. and one mm Hg to a constant weight of 186.8 grams of pale pink colored crystalline product.

E. Results and Product Analysis

The yield of isolated product based on sulfuric acid stoichiometry employed is 82.6%. HPLC analysis of a portion of the product reveals the presence of the following area percent distribution of components in their relative order of elution: phenol—0.10, 4,4'-dihydroxy-alpha-methylstilbene—87.50, unknown peak at higher retention time than 4,4'-dihydroxy-alpha-methylstilbene—0.28, 4,4'-dihydroxy-alpha-methylstilbene dimer A—7.70, unknown at slightly higher retention time than dimer A—1.38, 4,4'-dihydroxy-alpha-methylstilbene dimer B plus dihydroxy-alpha-methylstilbene isomer—2.74. Since the aforementioned HPLC analytical method does not resolve 1,2,2-tris(4-hydroxyphenyl)propane from the 4,4'-dihydroxy-alpha-methylstilbene peak, a separate method of HPLC analysis is employed and reveals the presence of none of this trisphenol. Differential scanning calorimetry of portions of the product (11.0 and 16.2 milligrams) using a heating rate of 10° C./min. from 30° C. to 300° C. under a nitrogen atmosphere flowing at 35 cubic centimeters per minute reveals a single sharp melting point endotherm with a minimum at 175.2° C. and an enthalpy of 126.9 joules per gram (average of two samples). High pressure liquid chromatography-mass spectrometry confirmed the structure of 4,4'-dihydroxy-alpha-methylstilbene (m/e parent radical cation and base peak=226), 4,4'-dihydroxy-alpha-methylstilbene dimer A (m/e parent radical cation=452, m/e base peak=227), dihydroxyl-alpha-methylstilbene isomer (m/e parent radical cation and base peak=226), 4,4'-dihydroxy-alpha-methylstilbene dimer B (m/e parent radical cation=452, m/e base peak=227). The dihydroxy-alpha-methylstilbene isomer and 4,4'-dihydroxy-alpha-methylstilbene dimer B peaks are not sufficiently resolved by the HPLC analysis for separate integration of each respective component. The high pressure liquid chromatography-mass spectrometry analysis was performed using a Finnigan SSQ-710 mass spectrometer interfaced to a Hewlett-Packard 1090M liquid chromatograph. A Keystone ODS column (250 mm by 4.6 mm) was used. The mobile phase gradient used was as follows with a flow set at 0.7 milliliters per minute: initial= 30% acetonitrile, 70% water; 15 minutes=55% acetonitrile, 45% water; 20 minutes=70% acetonitrile, 30% water; 25 minutes=95% acetonitrile, 5% water; 27 minutes=30% acetonitrile and 70% water. The diode-array detector was set at 220 nm and the signal was sent to the mass spectrometer data system. After passing through the diode-array detector, the liquid stream entered the mass spectrometer via a particle beam liquid chromatograph-mass spectrometer interface set at 60° C. Electron impact mass spectra of the eluted components were collected from 50 to 650 amu at 2 second intervals. The mass spectrometer source temperature was set at 250° C. Proton magnetic resonance spectroscopy and Fourier transform infrared spectrophotometric analysis additionally confirm the product structure.

COMPARATIVE EXPERIMENT A (Not an example of the present invention)

Synthesis of 4,4'-Dihydroxy-alpha-methylstilbene Using a 5:1:1 Mole Ratio of Phenol:Chloroacetone:Sulfuric Acid and Methylene Chloride as Solvent Phenol (941 grams, 10.0 moles), chloroacetone (191.6 grams, 2.0 moles) and methylene chloride (900 milliliters) are added to a 5 liter glass reactor equipped with a chilled water condenser, mechanical stirrer, nitrogen purge (one liter per minute), thermometer, dropping funnel and jacket for circulating coolant over the reactor exterior. Stirring commences concurrent with cooling of the reactant solution to −10° C. Concentrated sulfuric acid (196.4 grams, 2.0 moles) is added to the dropping funnel, then dropwise addition to the stirred reactant solution commences over a 70 minute period and so as to maintain the reaction temperature between −9° C. and −12° C. After 16 hours and 50 minutes of post reaction at −12° C., high pressure liquid chromatographic (HPLC) analysis of a portion of the product using a uv detector set at 254 nm reveals the presence of the following area percent distribution of components in their relative order of elution: phenolsulfonic acids—0.19, phenol—68.04, 1,2,2-tris(4-hydroxyphenyl)propane—0.85, 4,4'-dihydroxy-alpha-methylstilbene—1.68, 1,2-(4-hydroxyphenyl)-2-chloropropane—25.68, higher retention time compounds—0.698 plus 1.716 plus 1.145. At this time, chilled (7° C.) deionized water (1000 milliliters) is added to the stirred reaction product, inducing an exotherm to 0° C., then after two minutes of mixing, the opaque, pale pink colored product is recovered and divided equally into a pair of 2 liter glass separatory funnels. The contents of each separatory funnel are washed four times each with 500 milliliter portions of 45° C. deionized water. The combined organic layers are recovered and divided equally into a pair of 4 liter glass beakers. The contents of each beaker are stirred, deionized water (260 milliliters) is added and heating commences. Once a temperature of 80° C. is achieved, heating ceases and deionized water is added to each beaker in an amount sufficient to produce a total volume of 3.8 liters. The resultant crystalline slurry which forms is maintained with stirring for the next 16 hours at room temperature (23° C.). At this time, stirring is stopped and the crystalline product is recovered via filtration of the crystalline slurry then added to a glass beaker and combined therein with deionized water (one liter). Stirring and heating commence until the stirred slurry reaches 100° C. After 5 minutes at 100° C., the stirred slurry is filtered through a fritted glass filter. The product recovered from the filter is dried in a vacuum oven at 80° C. and one mm Hg to a constant weight of 285.5 grams of pale pink colored crystalline product. The yield of isolated product based on sulfuric acid stoichiometry employed is 63.2%. HPLC analysis of a portion of the product reveals the presence of the following area percent distribution of components in their relative order of elution: phenol—0,080, 4,4'-dihydroxy-alpha-methylstilbene—85.47, two unknown peaks at higher retention time than 4,4'-dihydroxy-alpha-methylstilbene—0.439 plus 0.946, 4,4'-dihydroxy-alpha-methylstilbene dimer A—9.48, two unknown peaks at higher retention time than 4,4'-dihydroxy-alpha-methylstilbene dimer A—0, 561 plus 0.125, 4,4'-dihydroxy-alpha-methylstilbene dimer B plus dihydroxy-alpha-methylstilbene isomer—1.98, three unknown peaks at higher retention time than 4,4'-dihydroxy-alpha-methylstilbene dimer B—0.339 plus 0.183 plus 0.158. Since the aforementioned HPLC analytical method does not resolve 1,2,2-tris(4-hydroxyphenyl)propane from the 4,4'-dihydroxy-alpha-methylstilbene peak, a separate method of HPLC analysis is employed and reveals the presence of none of this trisphenol. Differential scanning calorimetry of portions of the product (13.3 and 14.4 milligrams) using a heating rate of 10° C./min. from 30° C. to 300° C. under a nitrogen atmosphere flowing at 35 cubic centimeters per minute reveals a single sharp melting point endotherm with a minimum at 177.2° C. and an enthalpy of 120.8 joules per gram (average of two samples). High pressure liquid chromatography-mass o spectrometry confirmed the structure of 4,4'-dihydroxy-alpha-methylstilbene (m/e parent radical cation and base peak=226), 4,4'-dihydroxy-alpha-methylstilbene dimer A (m/e parent radical cation=452, m/e base peak=227), dihydroxy-alpha-methylstilbene isomer (m/e parent radical cation and base peak=226), 4,4'-dihydroxy-alpha-methylstilbene dimer B (m/e parent radical cation= 452, m/e base peak=227). The dihydroxy-alpha-methylstilbene isomer and 4,4'-dihydroxy-alpha-methylstilbene dimer B peaks are not sufficiently resolved by the HPLC analysis for separate integration of each respective component. The high pressure liquid chromatography-mass spectrometry analysis was performed using the method of Example 1. Proton magnetic resonance spectroscopy and Fourier transform infrared spectrophotometric analysis additionally confirm the product structure.

COMPARATIVE EXPERIMENT B (Not an example of the present invention)

Synthesis of 4,4'-Dihydroxy-alpha-methylstilbene Using a 10:1:1 Mole Ratio of Phenol:Chloroacetone:Sulfuric Acid and Methylene Chloride as Solvent Phenol (941 grams, 10.0 moles), chloroacetone (95.8 grams, 1.0 mole) and methylene chloride (1200 milliliters) are added to a 5 liter glass reactor equipped with a chilled water condenser, mechanical stirrer, nitrogen purge (one liter per minute), thermometer, dropping funnel and jacket for circulating coolant over the reactor exterior. Stirring commences concurrent with cooling of the reactant solution to −10° C. Concentrated sulfuric acid (98.2 grams, 1.0 mole) is added to the dropping funnel, then dropwise addition to the stirred reactant solution commences over a 40 minute period and so as to maintain the reaction temperature between −10° C. and −13° C. After 17 hours and 50 minutes of post reaction at −12° C., high pressure liquid chromatographic (HPLC) analysis of a portion of the product using a uv detector set at 254 nm reveals the presence of the following area percent distribution of components in their relative order of elution: phenolsulfonic acids—0.078, phenol—87.02, 1,2,2-tris(4-hydroxyphenyl)propane—0.383, 4,4'-dihydroxy-alpha-methylstilbene—0.871, 1,2-(4-hydroxyphenyl)-2-chloropropane—10.433, higher retention time compounds—0.913 plus 0.219. At this time, chilled (7° C.) deionized water (1000 milliliters) is added to the stirred reaction product, inducing an exotherm to −1° C., then after two minutes of mixing, the opaque, pale pink colored product is recovered and divided equally into a pair of 2 liter glass separatory funnels. The contents of each separatory funnel are washed four times each with 500 milliliter portions of 45° C. deionized water. The combined organic layers are recovered and divided equally into a pair of 4 liter glass beakers. The contents of each beaker are stirred, deionized water (260 milliliters) is added and heating commences. Once a temperature of 80° C. is achieved, heating ceases and deionized water is added to each beaker in an amount sufficient to produce a total volume of 3.8 liters. The resultant crystalline slurry which forms is maintained with stirring for the next 16 hours at room temperature (23° C.). At this time, stirring is stopped and the crystalline product is recovered via filtration of the crystalline slurry then added to a glass beaker and combined therein with deionized water (one liter). Stirring and heating commence until the stirred slurry reaches 100° C. After 5 minutes at 100° C., the stirred slurry is filtered through a fritted glass filter. The product recovered from the filter is dried in a vacuum oven at 80° C. and one mm Hg to a constant weight of 109.7 grams of pale pink colored crystalline product. The yield of isolated product based on sulfuric acid stoichiometry employed is 48.5%. HPLC analysis of a portion of the product reveals the presence of the following area percent distribution of components in their relative order of elution: phenol—0.094, 4,4'-dihydroxy-alpha-methylstilbene—92.26, 4,4'-dihydroxy-alpha-methylstilbene dimer A—6.34, one unknown peak at higher retention time than 4,4'-dihydroxy-alpha-methylstilbene dimer A—0.347, 4,4'-dihydroxy-alpha-methylstilbene dimer B plus dihydroxy-alpha-methylstilbene isomer—0.719. Since the aforementioned HPLC analytical method does not resolve 1,2,2-tris(4-hydroxyphenyl)propane from the 4,4'-dihydroxy-alpha-methylstilbene peak, a separate method of HPLC analysis is employed and reveals the presence of none of this trisphenol. Differential scanning calorimetry of portions of the product (11.3 and 12.3 milligrams) using a heating rate of 10° C./min. from 30° C. to 300° C. under a nitrogen atmosphere flowing at 35 cubic centimeters per minute reveals a broad endotherm with a minimum at 125.8° C. and an enthalpy of 22.8 joules per gram and a sharp melting point endotherm with a minimum at 184.7° C. and an enthalpy of 130.1 joules per gram (average of two samples). High pressure liquid chromatography-mass spectrometry confirmed the structure of 4,4'-dihydroxy-alpha-methylstilbene (m/e parent radical cation and base peak=226), 4,4'-dihydroxy-alpha-methylstilbene dimer A (m/e parent radical cation=452, m/e base peak= 227), dihydroxy-alpha-methylstilbene isomer (m/e parent radical cation and base peak=226), 4,4'-dihydroxy-alpha-methylstilbene dimer B (m/e parent radical cation=452, m/e base peak=227). The dihydroxy-alpha-methylstilbene isomer and 4,4'-dihydroxy-alpha-methylstilbene dimer B peaks are not sufficiently resolved by the HPLC analysis for separate integration of each respective component. The high pressure liquid chromatography-mass spectrometry analysis was performed using the method of Example 1. Proton magnetic resonance spectroscopy and Fourier transform infrared spectrophotometric analysis additionally confirm the product structure.

COMPARATIVE EXPERIMENT C (Not an example of the present invention)

Synthesis of 4,4'-Dihydroxy-alpha-methylstilbene Using a 5:1.0:0.1 Mole Ratio of Phenol:Chloroacetone:Sulfuric Acid using Methylene Chloride as Solvent Phenol (941 grams, 10.0 moles), chloroacetone (191.6 grams, 2.0 moles) and methylene chloride (900 milliliters) are added to a 5 liter glass reactor equipped with a chilled water condenser, mechanical stirrer, nitrogen purge (one liter per minute), thermometer, dropping funnel and jacket for circulating coolant over the reactor exterior. Stirring commences concurrent with cooling of the reactant solution to −10° C. Concentrated sulfuric acid (19.64 grams, 0.2 moles) is added to the dropping funnel, then dropwise addition to the stirred reactant solution commences over a 12 minute period and so as to maintain the reaction temperature between −10° C. and −12° C. After 17 hours and 46 minutes of post reaction at −12° C., high pressure liquid chromatographic (HPLC) analysis of a portion of the product using a uv detector set at 254 nm reveals the presence of the following area percent distribution of components in their relative order of elution: phenolsulfonic acids—0.03, chloroacetone—0.57, phenol—94.90, 1,2,2-tris(4-hydroxyphenyl)propane—0.330, 4,4'-dihydroxy-alpha-methylstilbene—1.81, 1,2-(4-hydroxyphenyl)-2-chloropropane— 2.14, higher retention time compounds—0.213. At this time, chilled (7° C.) deionized water (1000 milliliters) is added to the stirred reaction product, inducing an exotherm to 0° C., then after two minutes of mixing, the opaque, pale pink colored product is recovered and divided equally into a pair of 2 liter glass separatory funnels. The contents of each separatory funnel are washed four times each with 500 milliliter portions of 45° C. deionized water. The combined organic layers are recovered and divided equally into a pair of 4 liter glass beakers. The contents of each beaker are stirred, deionized water (260 milliliters) is added and heating commences. Once a temperature of 80° C. is achieved, heating ceases and deionized water is added to each beaker in an amount sufficient to produce a total volume of 3.8 liters. The product which results did not crystallize even after stirring for the next 16 hours at room temperature (23° C.).

The following Table is a summary of the preceeding Examples and Comparative Experiments.

| Example or Comp. Expt. | Melting Point °C. | Isolated Yield Based on Acid, % | HPLC Analysis, Area % | | |
|---|---|---|---|---|---|
| | | | DHAMS[a] | DHAMS[a] dimer A | DHAMS[a] dimer B |
| 1 | 187.4 | 83.0 | 92.42 | 6.46 | 0.367 |
| 2 | 189.0 | 84.2 | ND[d] | ND[d] | ND[d] |
| 3 | 175.2 | 82.6 | 87.5 | 7.70 | 2.74 |
| A | 177.2 | 63.2 | 85.47 | 9.48 | 1.98 |
| B | 184.7 | 48.5 | 92.26 | 6.34 | 0.719 |
| C | NA[c] | NCPO[b] | NA[c] | NA[c] | NA[c] |

[a]4,4'-dihydroxy-alpha-alkylstilbene.
[b]No crystalline product could be recovered.
[c]Not applicable since no crystalline product could be recovered.
[d]Not determined.

EXAMPLE 4

Synthesis of 4,4'-Dihydroxy-alpha-methylstilbene Using a Phenol:Chloroacetone:Sulfuric Acid Mole Ratio of 0.5:1.0:0.5

Phenol (188.2 grams, 2.0 moles) and chloroacetone (383.7 grams, 4.0 moles as chloroacetone) are added to a 5 liter glass reactor equipped with a chilled water condenser, mechanical stirrer, nitrogen purge (one liter per minute), thermometer, dropping funnel and jacket for circulating coolant over the reactor exterior. The chloroacetone is employed in a 0.5:1 mole ratio of phenol:chtoroacetone. Stirring commences concurrent with cooling of the reactant solution to −10° C. Concentrated sulfuric acid (19.6 grams, 0.20 mole) is added to the dropping funnel, then dropwise addition to the stirred reactant solution commences over a 24 minute period and so as to maintain the reaction temperature between −10° C. and −13° C. After 3 hours of post reaction at −13° C., high pressure liquid chromatographic (HPLC) analysis of a portion of the product using a uv detector set at 254 nm reveals the presence of the following area percent distribution of components in their relative order of elution: phenolsulfonic acids—0.07, chloroacetone—4.39, phenol—78.87, 4,4'-dihydroxy-alpha-methylstilbene—0.73, 1,2-(4-hydroxyphenyl)-2-chloropropane—14.33, higher retention time compounds—1.61.

A portion of the product was worked up using the method of Example 1. Differential scanning calorimetry of the product using the method of Example 1 shows a 188° C. melting point and an endotherm of 138 joules/gram enthalpy.

What is claimed is:

1. A process for preparing 4,4'-dihydroxy-alpha-alkylstilbenes and/or 4,4'-dihydroxy-alpha,alpha'-dialkylstilbenes said process comprising (A) reacting at a temperature of from about −20° C. to about 20° C. a mixture of
(1) at least one alpha-haloketone;
(2) at least one compound containing one phenolic hydroxyl group per molecule such that the mole ratio of phenolic hydroxyl group-containing compound(s):alpha-haloketone(s) is from, 0.1:1 to 1.9:1; and
(3) either (a) at least one strong protonic acid or (b) at least one Lewis acid or (c) any combination thereof; wherein the mole ratio of component (A2):component (A1):component (A3) is from about 0.1:1:0.0026 to about 1.9:1:0.95;

(B) substantially removing or neutralizing any residual acidic materials from the product produced in step (A); and (C) dehydrohalogenating the product retained from step (B).

2. The process of claim 1 comprising the additional step of recovering the desired 4,4'-dihydroxy-alpha-alkylstilbene and/or 4,4'-dihydroxy-alpha,alpha'-dialkylstilbene product from the product resulting from step (C).

3. The process of claim 2 wherein (i) the alpha-haloketone in (A) is represented by Formula III

Formula III wherein $R^3$ is hydrogen or a hydrocarbyl group having from one to about 8 carbon atoms; $R^4$ is a hydrocarbyl group having from one to about 8 carbon atoms; and X is a halogen atom;

(ii) the phenolic hydroxyl group-containing compound in (A) is represented by Formula I

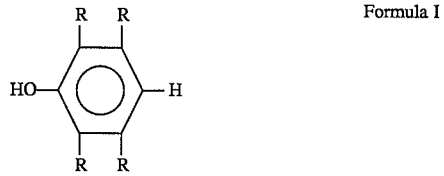

Formula I wherein each R is independently hydrogen or a hydrocarbyl or hydrocarbyloxy group having from one to about 12 carbon atoms, a halogen atom, a nitro group, a nitrile group, or a —CO—$R^1$ group; and $R^1$ is hydrogen or a hydrocarbyl group having from one to about 12 carbon atoms;

(iii) the mole ratio of component (A2):component (A1) is from about 0.5:1 to about 1.85:1;

(iv) the reaction temperature is from about −20° C. to about 20° C.;

(v) component (A3) is a strong protonic acid selected from the group consisting of sulfuric acid, sulfuric acid containing sulfur trioxide, sulfonic acid form cation ion exchange resin (polystyrene lightly crosslinked with divinylbenzene), methanesulfonic acid, p-toluenesulfonic acid, hydrogen chloride, or any combination thereof; and (vi) the mole ratio of component (A2):component (A1):component (A3) is from about 0.5:1:0.020 to about 1.85:1:0.617.

4. The process of claim 3 wherein (i) component (A1) is chloroacetone, bromoacetone, 3-chlorobutan-2-one, 1-chloropentan-2-one, 2-chloropentan-3-one, 3-chloropentan-2-one, 4-methyl-3-chloropentan-2-one, 4-methyl-2-chloropentan-3-one, 4-methyl-1-chloropentan-2-one, 1-chlorooctan-2-one, or any combination thereof;

(ii) the mole ratio of component (A2):component (A1) is from about 1:1 to about 1.80: 1;

(iii) the reaction temperature is from about −15° C. to about 10° C.;

(iv) component (A2) is phenol, 2,6-dimethylphenol, 2,6-diethylphenol, 2,6-dibromophenol, 2,6-dichlorophenol, 2,6-difluorophenol, 2,6-dimethoxyphenol, 2,6-diethylphenol, 3,5-dimethylphenol, 2-nitrophenol, 2-cyanophenol, 2-methylphenol, 3-methylphenol, 2-phenylphenol, 2-cyclohexylphenol, 2-octylphenol, 2-methyl-6-chlorophenol, 2-methoxy-6-chlorophenol, 2,3,5,6-tetramethylphenol, or any combination thereof;

(v) component (A3) is sulfuric acid; and (vi) the mole ratio of component (A2):component (A1):component (A3) is from about 1:1:0.1 to about 1.80:1:0.225.

5. The process of claim 4 wherein (i) component (A1) is chloroacetone; and (ii) component (A2) is phenol.

6. A process for preparing 4,4'-dihydroxy-alpha-alkylstilbenes or 4,4'-dihydroxy-alpha,alpha'-dialkylstilbenes wherein said process comprises (A) reacting at a temperature of from about −20° C. to about 20° C. a mixture of
  (1) at least one alpha-haloketone;
  (2) at least one aromatic compound containing one alkoxy group per molecule such that the mole ratio of alkoxy group-containing aromatic compound(s):alpha-haloketone(s) is from 0.1:1 to 1.9:1; and
  (3) either (a) at least one strong protonic acid or (b) at least one Lewis acid or (c) any combination thereof;
  wherein the mole ratio of alkoxy group-containing aromatic compound(s):alpha-haloketone(s):strong protonic acid or Lewis acid is from about 0.1:1:0.0026 to about 1.9:1:0.95;

(B) substantially removing or neutralizing any residual acidic materials from the product of step (A);

(C) dehydrohalogenating the product retained from step (B); and (D) dealkylating the product resulting from step (C).

7. The process of claim 6 comprising the additional step of recovering the desired 4,4'-dihydroxy-alpha-alkylstilbene or 4,4'-dihydroxy-alpha,alpha'-dialkylstilbene product from the product resulting from step (D).

8. The process of claim 7 wherein (i) the alpha-haloketone in (A) is represented by Formula III

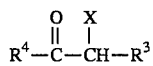

Formula III wherein $R^3$ is hydrogen or a hydrocarbyl group having from one to about 8 carbon atoms; $R^4$ is a hydrocarbyl group having from one to about 8 carbon atoms; and X is a halogen atom;

(ii) the alkoxy group-containing aromatic compound(s) in (A) is represented by Formula II

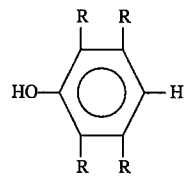

Formula II wherein each R' is independently hydrogen or a hydrocarbyl group having from one to about 12 carbon atoms, a halogen atom, a nitro group, a nitrile group, or a —CO—$R^1$ group; $R^1$ is hydrogen or a hydrocarbyl group having from one to about 12 carbon atoms; and $R^2$ is a hydrocarbyl group having from one to about 6 carbon atoms;

(iii) the mole ratio of component (A2):component (A1) is from about 0.5:1 to about 1.85:1;

(iv) the reaction temperature is from about −20° C. to about 20° C.;

(v) component (A3) is a strong protonic acid selected from the group consisting of sulfuric acid, sulfuric acid containing sulfur trioxide, sulfonic acid form cation ion exchange resin (polystyrene lightly crosslinked with divinylbenzene), methanesulfonic acid, p-toluenesulfonic acid, hydrogen chloride, or any combination thereof (vi) the mole ratio of component (A2):component (A1):component (A3) is from about 0.5:1:0.020 to about 1.85:1:0.617.

9. The process of claim 8 wherein (i) component (A1) is chloroacetone, bromoacetone, 3-chlorobutan-2-one, 1-chloropentan-2-one, 2-chloropentan-3-one, 3-chloropentan-2-one, 4-methyl-3-chloropentan-2-one, 4-methyl-2-chloropentan-3-one, 4-methyl-1-chloropentan-2-one, 1-chlorooctan-2-one, or any combination thereof;

(ii) the mole ratio of component (A2):component (A1) is from about 1:1 to about 1.80:1;

(iii) the reaction temperature is from about −15° C. to about 10° C.;

(iv) component (A2) is anisole, phenetole, 2,6-dimethylanisole, 2,6-diethylanisole, 2,6-dibromoanisole, 2,6-dichloroanisole, 2,6-difluoroanisole, 3,5-dimethylanisole, 2-nitroanisole, 2-cyanoanisole, 2-methylanisole, 3-methylanisole, 2-phenylanisole, 2-cyclohexylanisole, 2-octylanisole, 2-methyl-6-chloroanisole, 2-methoxy-6-chloroanisole, 2,3,5,6-tetramethylanisole, or any combination thereof;

(v) component (A3) is sulfuric acid; and (vi) the mole ratio of component (A2):component (A1):component (A3) is from about 1:1:0.1 to about 1.80:1:0.225.

10. The process of claim 9 wherein (i) component (A1) is chloroacetone; and (ii) component (A2) is anisole.

11. A 4,4'-dihydroxy-alpha-alkylstilbene or 4,4'-dihydroxy-alpha,alpha'-dialkylstilbene resulting from the process of claims 1, 2, 3, 4, 5, 6, 7, 8, 9 or 10.

* * * * *